(12) United States Patent
Piatrou et al.

(10) Patent No.: US 10,674,972 B1
(45) Date of Patent: Jun. 9, 2020

(54) OBJECT DETECTION IN FULL-HEIGHT HUMAN X-RAY IMAGES

(71) Applicant: ADANI Systems, Inc., Alexandria, VA (US)

(72) Inventors: Vadzim A. Piatrou, Minsk (BY); Vladimir N. Linev, Minsk (BY); Iryna L. Slavashevich, Minsk (BY); Dmitry V. Pozdnyakov, Minsk (BY)

(73) Assignee: Adani Systems, Inc., Alexandria, VA (US)

( * ) Notice: Subject to any disclaimer, the term of this patent is extended or adjusted under 35 U.S.C. 154(b) by 72 days.

(21) Appl. No.: 16/150,436

(22) Filed: Oct. 3, 2018

(51) Int. Cl.
*A61B 6/00* (2006.01)
*G01N 23/04* (2018.01)
*G01T 1/16* (2006.01)

(52) U.S. Cl.
CPC ............ *A61B 6/4208* (2013.01); *A61B 6/461* (2013.01); *G01N 23/04* (2013.01); *G01T 1/16* (2013.01)

(58) Field of Classification Search
CPC ...... A61B 6/4208; A61B 6/461; G01N 23/04; G01T 1/16; G06T 7/11; G06T 7/12; G06T 7/143; G06F 19/321; G06K 9/42; G06K 9/3233; G06N 3/084
See application file for complete search history.

*Primary Examiner* — Leon Viet Q Nguyen
(74) *Attorney, Agent, or Firm* — Bardmesser Law Group (57) ABSTRACT

Detecting hidden objects on a human body includes acquiring an incoming X-ray image of the human body passing through a penetrating X-ray scanner; generating additional images based on the incoming image by performing logarithmic or saliency transformations or contrasting of the incoming image; obtaining maps for all objects and known object classes, the maps show which pixels correspond to objects or to background, by passing the incoming and the additional images through a neural network with a deep Segnet-U-Net architecture optimized for overlapping object detection with long skip connections before each downsampling layer of the neural network; using the maps, identifying unknown objects in the incoming image by recognizing all objects/objects of known classes, excluding previously classified objects from the known classes from segmented non-anatomic areas; segmenting the incoming image of the human body into multiple parts; and identifying parts containing objects belonging to both the known and unknown classes.

6 Claims, 11 Drawing Sheets

CONVENTIONAL ART

OBJECT DETECTION IN FULL-HEIGHT HUMAN X-RAY IMAGES

BACKGROUND OF THE INVENTION

Field of the Invention

The present invention relates to automatic identification of hidden or dangerous objects on a human body, such as when scanning people at security checkpoints.

Description of the Related Art

Microwave or X-ray human body scanners with penetrating or reflected radiation, or personal scanners, are used in secure areas, such as airports, to detect illegal or prohibited objects concealed on the human body and/or inside the human body, without a manual pat-down or search. Such scanners display a body image of the searched person on the operator's screen, and the operator has to visually assess it for any illegal items.

Today, high airport traffic requires automated methods for searching for illegal items on the human body and/or in its internal cavities to be used, with minimum input from the operator.

Personal X-ray scanners based on penetrating radiation used in airports and other transportation facilities allow prevention of illegal movement of dangerous objects concealed on the human body or in its internal cavities. Unlike manual image inspection, automated algorithms for analysis of scanned images for illegal items offer the following improvements over conventional image checks by an operator:

- throughput of the scanner is increased by an automated algorithm that takes considerably less time than visual check by an operator (in this case, the operator's input is required only to confirm dangerous object alerts generated by the algorithm);
- consistent precision, as the effects of tiredness are eliminated;
- all data from the image is used including analysis of the private body parts that may not be displayed to the operator for privacy protection reasons;
- scanning costs are improved, since operators can be less qualified, and one operator is able to service several scanners.

Many publications, listed below and incorporated herein in their entirety, deal with object search in images. However, the approaches described therein face many limitations when applied to the problem of airport scanning.

J. Sun (2011) discloses methods for detection of high-contract objects in images using sets of local, regional and global characteristics. However, that method cannot be applied to object search on a human body, since human bones have relatively higher contrast than other body parts, while certain non-anatomic (foreign) objects have lower contrast and, therefore, cannot be reliably distinguished from the rest of the body.

Mery (2011) proposes a method for detecting welding defects by a sliding window method. However, while welding seams are relatively homogeneous, the human body area has a lot of anatomic abnormalities, which may result in high noise and many false positives.

Saisan (2013) teaches that individual objects in an image can be segmented and then classified as corresponding to target objects based on their geometric properties. Applying that method to the problem at hand may be difficult, as objects cannot be reliably classified based on their geometric properties only, if that object type wasn't used during the algorithm development.

Vaidya (2014) teaches an automated algorithm for searching objects concealed on a human body using microwave scanners, wherein a series of body images is analyzed for illegal objects. However, that algorithm cannot be applied to searching for objects in human X-ray images. This limitation is due to the fact that the algorithm is based on searching for "valleys" and "mountains" on a relatively homogeneous background formed by the human body surface, while X-ray scanners using penetrating radiation produce highly inhomogeneous images, as there are multiple anatomic abnormalities, such as bones, inside the human body.

Piatrou (2017) presents an algorithm for detection of drug packets/capsules in human stomach from full-height X-ray images. However, that algorithm is limited specifically to detecting such packets in the stomach area only.

Kumar, P. et al., *U-SegNet: Fully Convolutional Neural Network based Automated Brain tissue segmentation Tool*, arXiv preprint arXiv:1806.04429 (2018) proposes a hybrid of two widely used deep learning architectures, namely Segnet (Badrinarayanan) and U-Net (Ronneberger), to enhance segmentation of brain tissues. The resulting architecture (a deep Segnet-U-Net architecture) applies long skip connections from U-Net to Segnet architecture for more efficient parsing of fine-grained multiscale structure, in order to better identify tissue borders. However, it cannot be used to solve the proposed problem, since detection of objects belonging to various classes in a non-homogeneous human body requires more layers and long skip connections than the architecture actually has. Also, this architecture is limited to detecting only two classes of non-overlapping tissues, which is insufficient for the problem at hand. At the same time, the task of object detection in X-ray images cannot amount just to semantic segmentation, since every object that is not a part of the body has to be detected and then classified.

Abedini (2017) proposes a method for determining borders by segmenting the image. That method is based on training of several classifiers, so as to classify each pixel as a damaged one compared to normal pixels, where each such classifier is trained with a specified resolution range. However, that method allows to determine the borders of a specific damage only and cannot be used for classification.

J. Sun (2018) and G. V. Castano (2018) describe methods for fast and accurate object detection and classification in images. However, since they are closely bound to detection of objects form specific classes, those methods are not designed for detection of objects that do not belong to any class but are not a part of the background either—in other words, the specific challenges of a security checkpoint in an airport environment.

SUMMARY OF THE INVENTION

The invention relates to detection of contraband, and of hidden and dangerous objects, in full-height human images that substantially overcomes one or more disadvantages of the related art.

In an exemplary embodiment, a method for detecting and recognizing hidden objects on a human body includes the steps of acquiring an incoming X-ray image of the human body passing through a penetrating X-ray scanner; generating additional images based on the incoming image by performing logarithmic or saliency transformations or contrasting of the incoming image; obtaining maps for all objects and known object classes, wherein the maps show which pixels correspond to objects and which pixels correspond to background, by passing the incoming and the additional images through a neural network with a deep Segnet-U-Net architecture that is optimized for overlapping object detection with a long skip connections before each downsampling layer of the neural network; using the maps, identifying unknown objects in the incoming image by recognizing all objects and objects of known classes, and excluding previously classified objects from the known classes from an entire set of segmented non-anatomic areas; segmenting the incoming image of the human body into multiple parts; and identifying parts containing objects belonging to both the known and unknown classes. Optionally, the neural network is trained by using a dataset of images of people passing through a penetrating X-ray scanner; generating additional images for dataset images by performing the transformations of the images; adding logarithmic brightness values of images containing individual objects to logarithmic brightness values of original human images in order to enlarge the dataset with forbidden objects; using parts of images of human bodies to train the neural network to improve recognition of objects; using a neural network with the deep Segnet-U-Net architecture to identify known and unknown objects and the classes to which they belong; and training the neural network using the images from the dataset and maps for all objects and known classes in order to detect and classify previously unidentified classes of objects.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF Description of the Attached Figures

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

In order to solve the problem of detection of objects concealed on a human body using an X-ray scanner, it is proposed to complement original images with additional ones, that are derived from the original image, such as a logarithmic image, a contrasted image, and a saliency map, see also copending U.S. patent application Ser. No. 15/427, 475, incorporated herein by reference in its entirety.

A logarithmic image reflects the information on how much penetrating radiation has been absorbed by various body parts and objects. Contrasted images allow to obtain better rendering of smaller details, which results in higher information value. A saliency map is an image processing method that allows to distinguish objects of a specified scale.

Then, a neural network trained with these images gives as a result a multi-channel abnormality map attesting to the degree the system is assured that the given pixels belong to particular objects. The abnormality map is separated into classes by channel, which are then analyzed separately.

A class that encompasses all non-anatomic (foreign) objects is a special class among obtained maps. Other classes include specific object types that have significance for detection, such as clothing or dangerous objects, as the former can be hidden from the operator, and the latter have to be highlighted on the screen and specifically communicated to the operator.

An improvement of the claimed solution is a method for detection of objects that do not belong to any class specified during the algorithm development, i.e., belonging to a class of "unknown" objects. Such "unknown" objects are detected by excluding objects of certain classes from the all objects map.

The next step in the algorithm is segmentation of a human body into areas, such as background, head, upper body, lower body, left arm, right arm, left leg, and right leg. Then, each body area is associated with a threat level depending on the types of objects that have been detected there.

Figure 1:
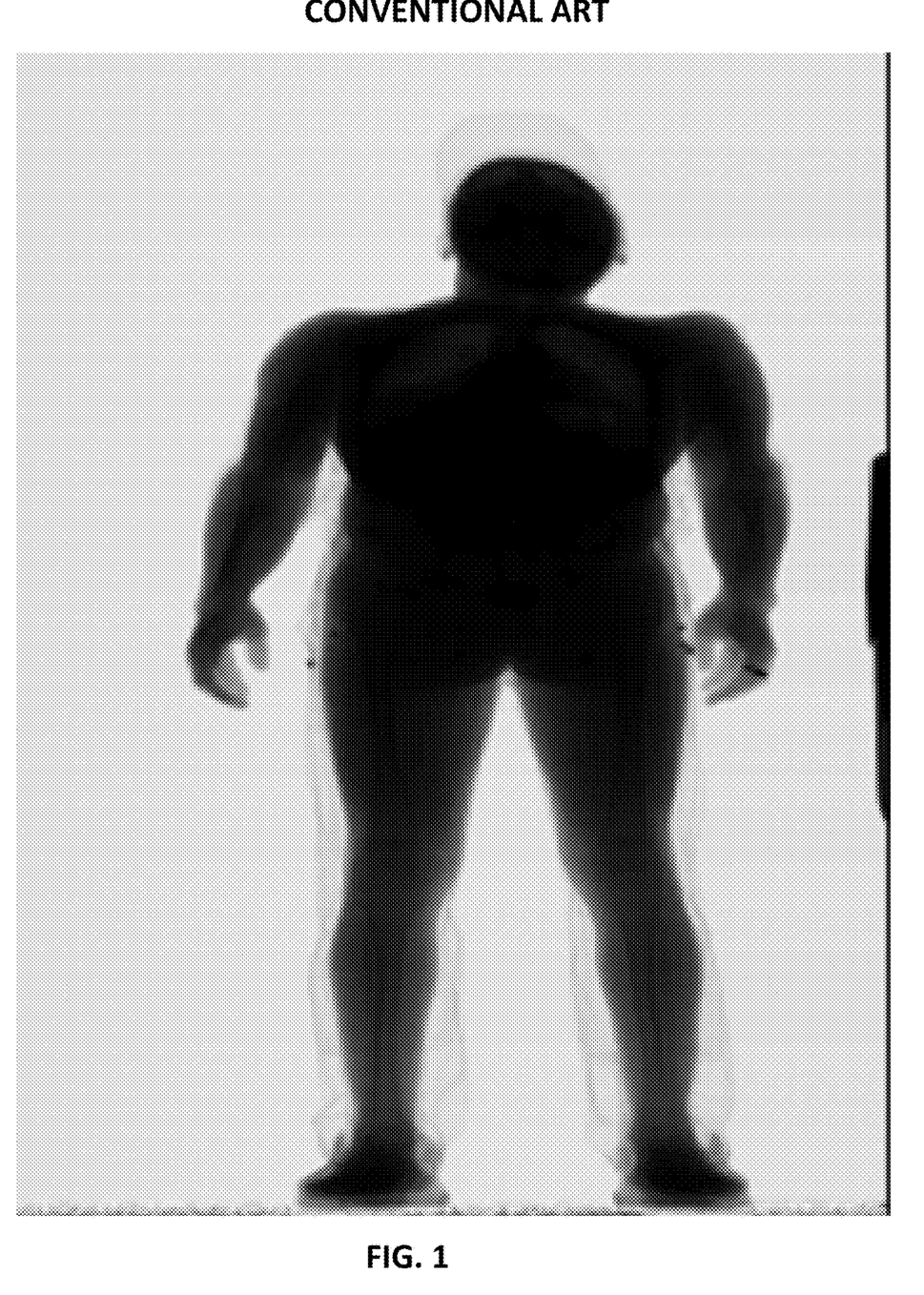
FIG. 1 is a sample image to be processed by the present algorithm.
Figure 2:
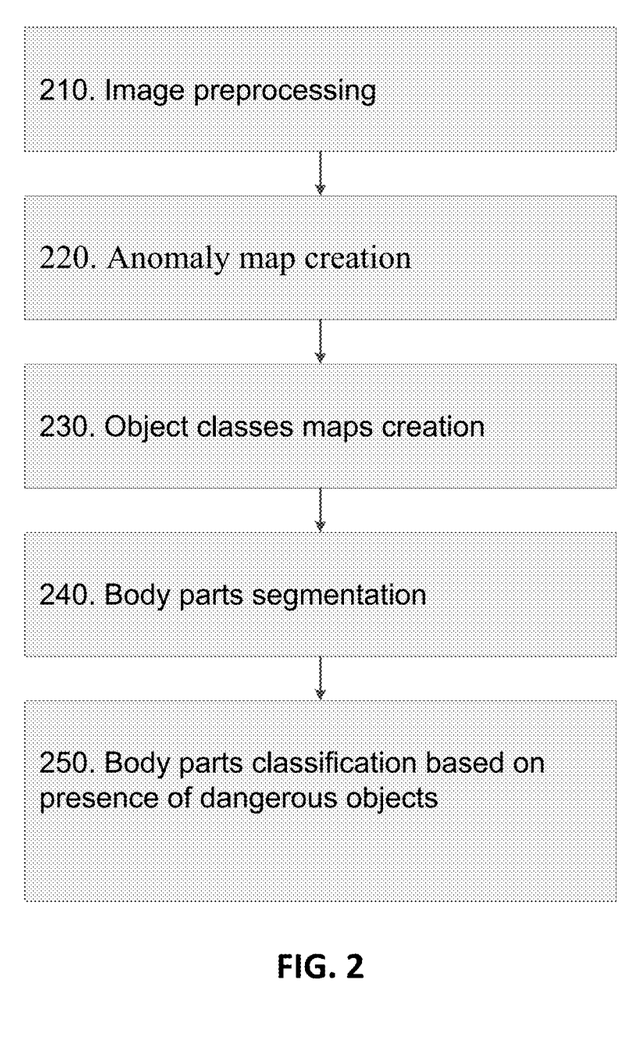
FIG. 2 is the flowchart of the object search algorithm.

FIG. 2 is the flowchart of the proposed algorithm of the present application. Using this algorithm, initial images of people (see FIG. 1) can be analyzed for objects, including prohibited ones. Also, each segmented body area can be classified based on whether it contains dangerous objects or not.

In step 210, an image to be analyzed is uploaded into the algorithm, and its data are prepared for further processing. For more details on this step, see FIG. 3.

Then, in step 220, the neural network, that was trained with the images, composes a multi-channel abnormality map attesting to the degree the system is assured that the pixels in the processed image belong to objects.

In step 230, the abnormality map is separated into classes by channel, which are then analyzed separately. A class that encompasses all non-anatomic (foreign) objects is a special class among obtained maps. Other classes are classes including specific object types that have significance for detection, such as clothing or dangerous objects, as the former can be hidden from the operator, and the latter have to be highlighted on the screen and specifically communicated to the operator. Electronic devices, that may have restrictions on use, may make up a separate class.

Dangerous object class may be replaced with a series of classes corresponding to various dangerous objects, such as firearms, melee weapons, explosives, etc.

Then, in step 240, the algorithm segments the human body into areas, such as background, head, upper body, lower body, left arm, right arm, left leg, and right leg.

Finally, in step 250, each body area is associated with a threat level depending on the types of objects that have been detected there. For instance, if a given body area contains dangerous objects, the operator is notified that this area is dangerous.

Figure 3:
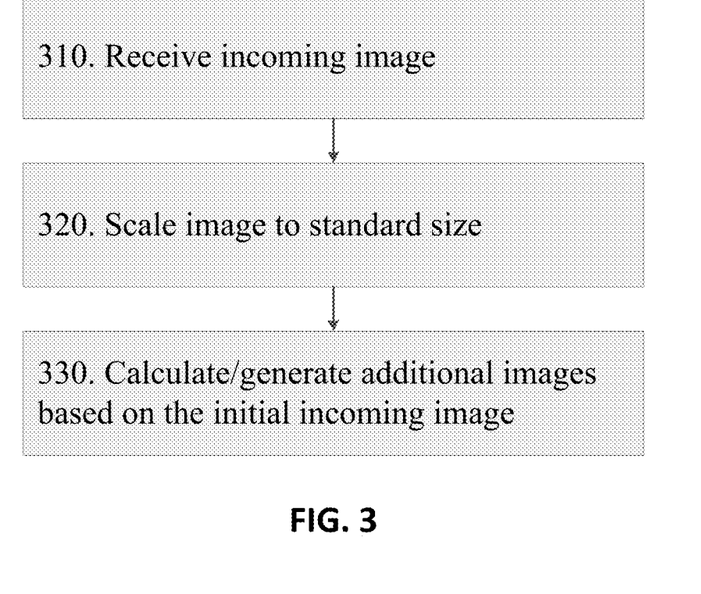
FIG. 3 illustrates data preparation for the algorithm.

FIG. 3 is the flowchart of the steps of the algorithm, where an image to be analyzed is uploaded, and its data are prepared for further processing. After the input image has been uploaded (step 310), it is scaled up to the standard size (step 320). Then, the input image is processed to obtain the following additional images (step 330):

a logarithmic image that reflects the physical information on how much penetrating radiation has been absorbed by various body parts;

an inverted logarithmic image that reflects the information on effective thickness of various body parts;

a saliency map that allows objects of specified size to be distinguished; and a contrasted image that allows to discern smaller details.

The original input image is bound to the settings of a specific instrument, and its data are poorly normalized by the intensity range, therefore, a logarithmic image suits better. A signal logarithm can be taken using the following formula:

$$\text{Log}(i) = \frac{\ln(1+i)}{\ln(1+\max)} \Box \max,$$

where i is the input signal level, and max is the maximum input signal level.

Figure 4:
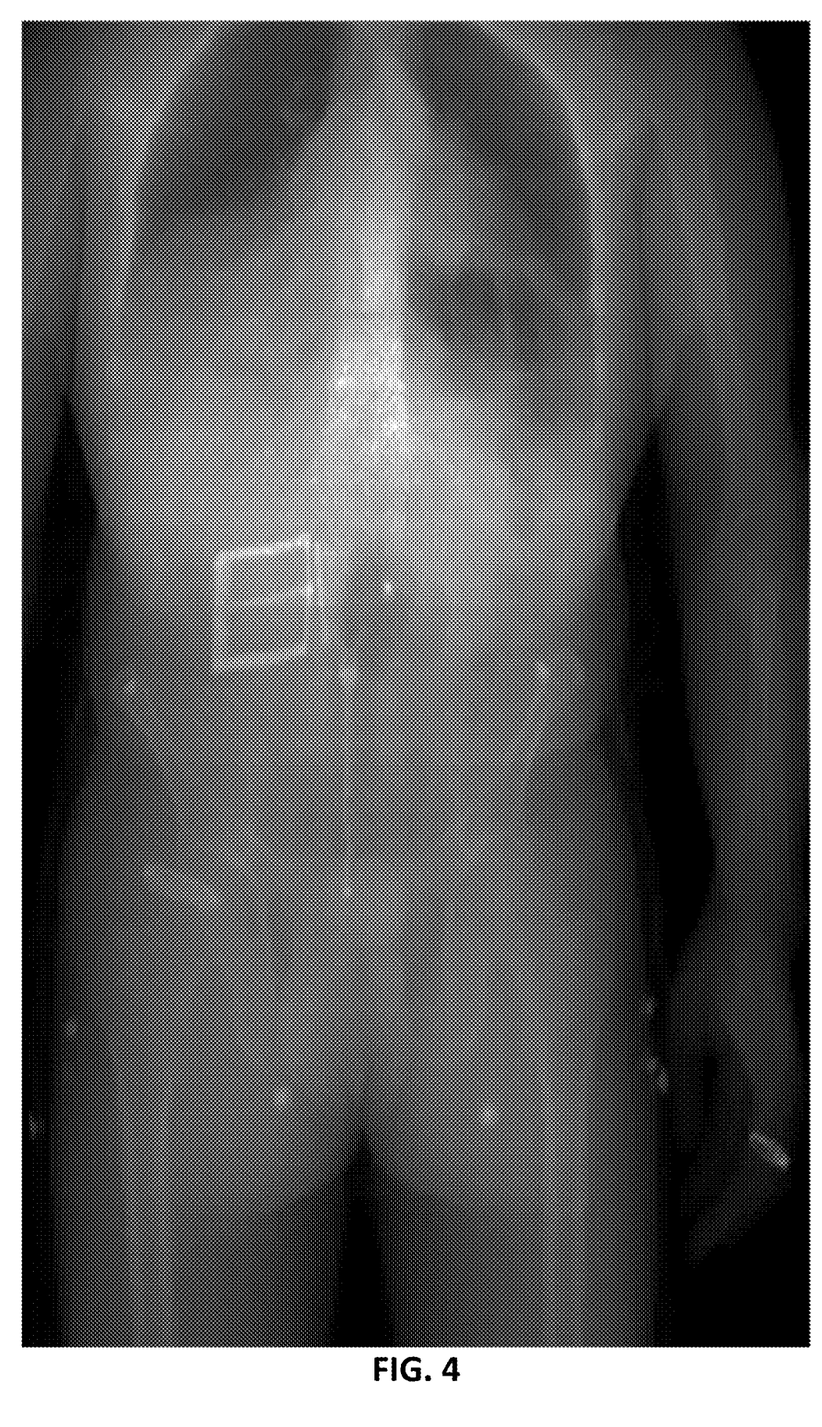
FIG. 4 is a sample inverted logarithmic image.

The formula for an inverted logarithmic signal is as follows:

$i \text{ Log}(i) = \log bg - \text{Log}(i)$.

where i is the input signal level, and logbg=Log(bg) is the logarithmic background signal (bg) level. FIG. 4 shows a sample image.

A saliency map results from image being processed based on the human attention system (Montabone and Soto, 2010). According to this system, when analyzing complex scenes, human visual perception sequentially focuses on different parts of the image. The algorithm may use saliency maps with scales fitted to the sizes of objects to be detected.

Image contrasting (see Zuiderveld, 1994 or Yu and Bajaj, 2004) is an image processing procedure that allows to achieve better local contrast between neighboring areas of an image. The methods are based on obtaining the local statistics of minimum, maximum and mean values for each small image area, which will then be used when redistributing pixel intensities within these areas.

To train the neural network, one or several image types are used, that have been prepared following the flowchart in FIG. 3, as described above. When several images are used, they may be provided to the neural network input as a multichannel image. However, the neural network also requires that object to be detected are marked, for training.

The objects may be marked both manually and using auxiliary object detection algorithms. When auxiliary algorithms are used, the image may be processed according to the sequence illustrated by FIG. 5.

Figure 5:
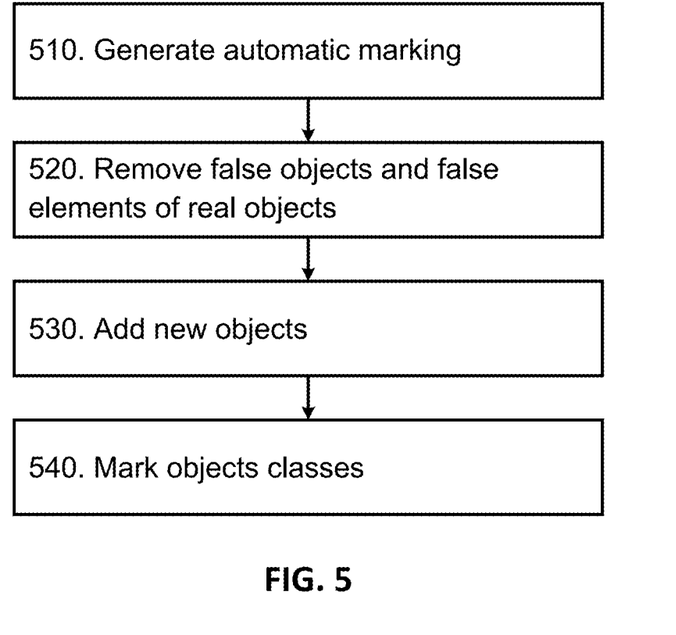
FIG. 5 illustrates data marking for neural network training.

First, the data to be used for neural network training are marked using auxiliary algorithms (510). Then, false objects and false parts of real objects are removed from the resulting marking (520). Then, new objects that have been missed by the auxiliary algorithms are added to the cleared-up marking (530). Finally, all objects are marked with classes (540).

Figure 6:
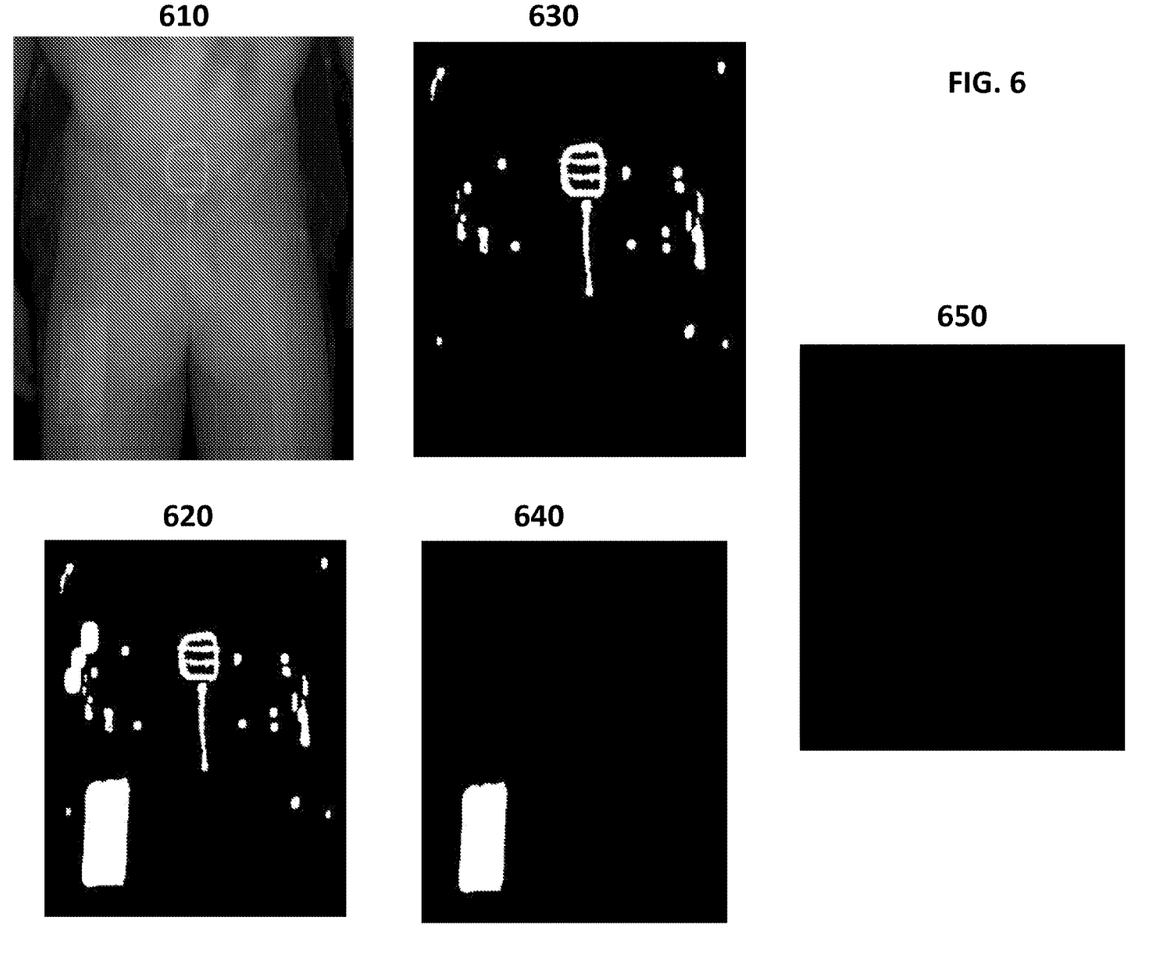
FIG. 6 is a sample part of an inverted logarithmic image, containing maps that have been marked to train the neural network to search objects, with the image part (on the top left) and marked object maps.

As a result, segmentation maps (see FIG. 6) have to be generated for each image 610 from the training and test bases that are used for training. The following object maps can be generated:

all objects map (620);
clothing map (630);
electronic device map (640);
dangerous object map (650).

It should be noted that "unknown" object maps are added only to the all object map. Further, such objects will be detected by excluding objects of known classes (e.g., guns, knives, etc.) from the all objects map. Three balls in the center-left part of the image 610 are an example of an unknown objects.

Figure 7:
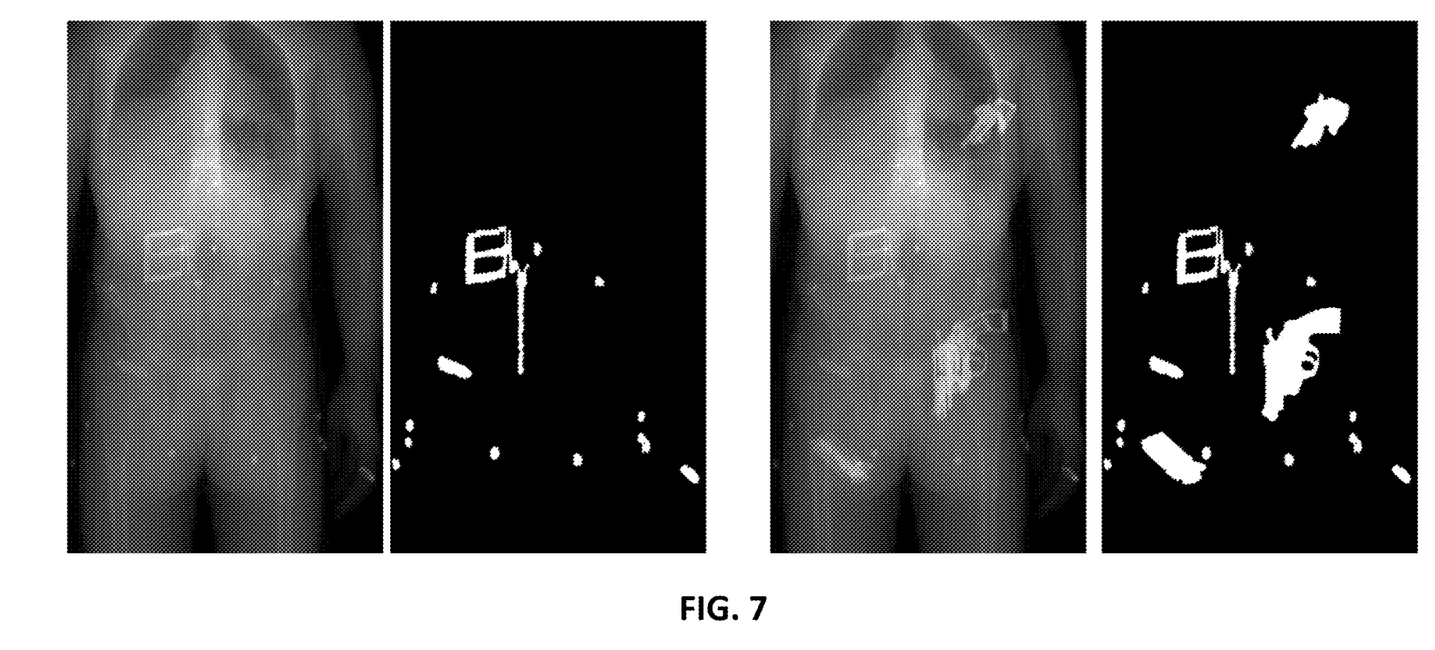
FIG. 7 illustrates exemplary overlaying of an inverted logarithmic image and object map with dangerous objects from the bases of different X-ray devices, where exemplary image and map without dangerous objects are shown on the left, and the image and map after overlaying of dangerous objects are shown on the right.

Since not only regular objects, such as clothing or electronic devices, that often appear on images have to be detected, but also dangerous objects, that appear on isolated images, in order to enhance their detection, an object base of a different X-ray scanner may be required, which encountered such objects. FIG. 7 is a sample image illustrating an ordinary image overlaid with dangerous objects (two handguns and a knife) from the base of a different scanner.

In order to effectively increase the image base and dangerous object base, the images were augmented by:

horizontal mirroring;
rotating by various angles (dangerous objects only);
intensity changes through gamma-adjustment, division/multiplication, contrasting, or smoothing; and
scaling.

In order to enhance algorithm interaction with noisy and low-contrast images, a small number of images from train set have been specially treated with gaussian noise.

Original images have fixed sizes, but smaller parts may be clipped from them for training purposes, so that a single batch for neural network training includes as many images as possible. It is important, as by complex image clips provide for a better training of the neural network. Final testing can be run on both full-size images and image clips.

Architecture of the Neural Network

Figure 8:
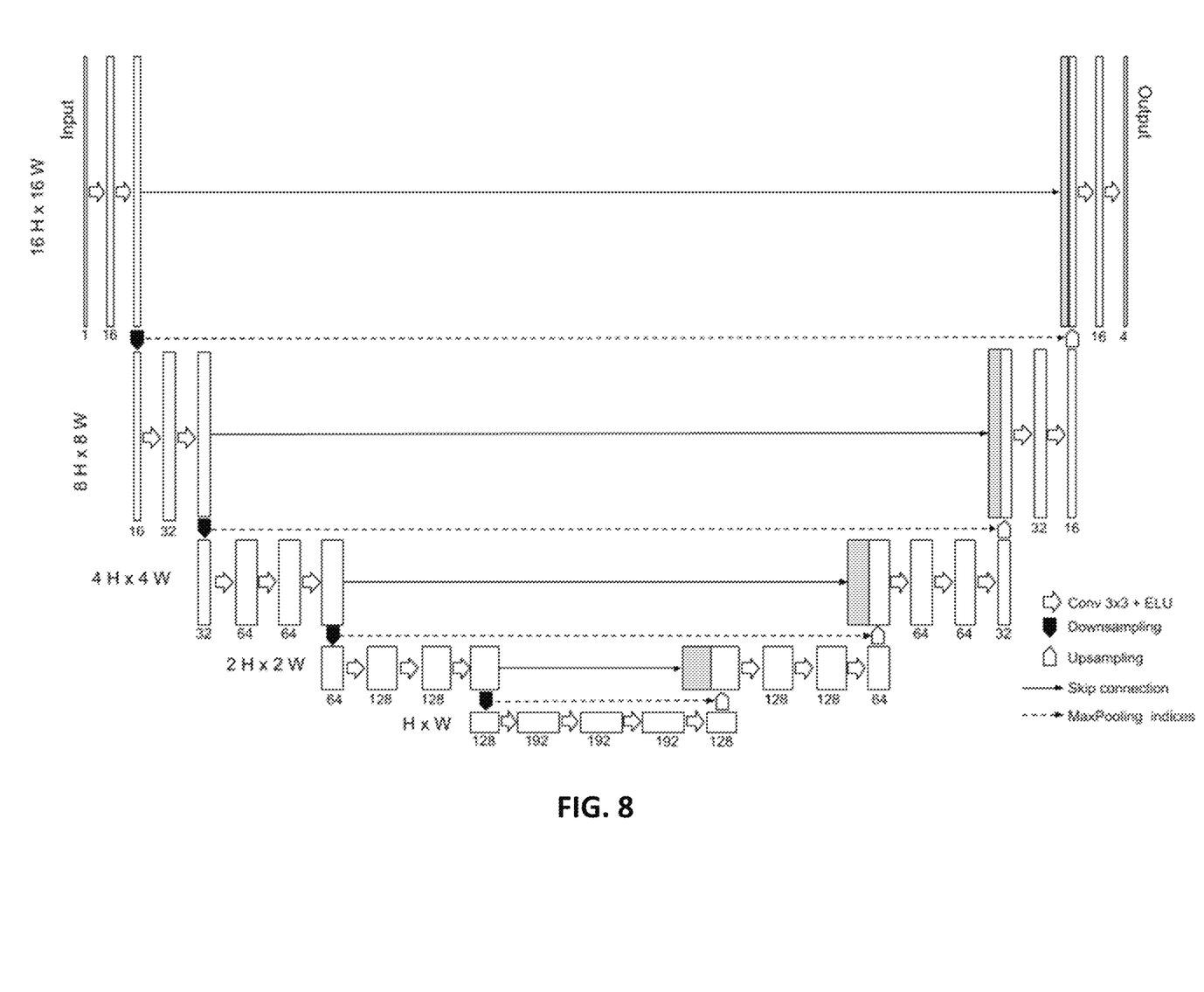
FIG. 8 shows the architecture of the neural network for detecting objects on a human body in X-ray images.

The model of the neural network is based on the combination of SegNet [Badrinarayanan] and U-Net [Ronneberger] architectures. SegNet provided the architecture with maximum pooling layers (MaxPooling), wherein indexes of maximum elements are passed to the second half of the neural network, and completely symmetrical structure. U-Net provided the architecture with long skip connections, wherein characteristics are passed from the encoder to the decoder for better restoration of high-resolution details. FIG. 8 illustrates the model of the neural network in use.

Unlike models mentioned above, ELU (Exponential Linear Unit) activations are used, along with less filters in layers (see FIG. 8), because the data are more homogeneous in their spatial dimensions than in other implementations of semantic segmentation. Each convolutional filter in the network has the dimensions of 3×3 pixels. There are 24 convolutional layers in total.

At the input of the neural network, there may be provided a single-channel or multi-channel image of standardized size (610).

The network comprises convolutional layers, ELU activations and maximum aggregation in the first half, where pooling results in gradual decrease of spatial dimensions of characteristics and increase of their channel quantities (see FIG. 8). In the first half (encoder), there are four units with different combinations of convolutional layer and ELU activation pairs: units 1 and 2 contain two pairs each; units 3 and 4 contain three pairs each. The last layer in each unit transfers the characteristics to a symmetrical convolution layer in the decoder, where it is combined with characteristics in decoder. Also, at the end of each encoder unit, there is a maximum pooling layer that decreases spatial dimensions of characteristics transferred over the network by half. Maximum element indexes are transferred from said layer to a symmetrical upscaling layer in the decoder. Another important aspect of the network is that the number of channels in convolutional layers immediately following the maximum pooling layer is consecutively increased. Therefore, the "width" of the neural network is increased gradually along the move towards the center.

The four encoder units are followed by four pairs of convolutional layers and ELU activations in the central part, with the increased number of channels after the first pair and equally decreased number of channels after the third pair.

Long skip connections and indices of maximum elements from the pooling layers are passed from the left half of the network to its right half. The right half of the network is symmetrical to its left half and comprises convolutional layers, ELU activations and upsampling operations. This half also comprises four units with different combinations of convolutional layer and ELU activation pairs: the first two units contain three pairs each, and the remaining two units contain two pairs each. Each of those units is preceded with an upsampling layer that obtains maximum element indices from the encoder and increases characteristics spatial size by two. After upsampling, the resulting characteristics are concatenated with the characteristics passed from the encoder, and then are sent to the convolution and activation units. The number of decoder channels is reduced on the last convolutional layer in each unit.

At the output of the neural network, there will be a multi-channel image with the same spatial dimensions as the input image. Each image channel corresponds to the abnormality map of a certain class. The resulting maps allow to obtain an object map by selecting a necessary threshold. One of the output channels is the all object map (620), while other channels are maps of specific classes, except for the unknown object class. It should be noted that "unknown" objects are detected by excluding all other maps from the all object map.

Detection level may be assessed well with F1 score. This generalized function for detection quality is calculated through the rates of detected objects (det) and false objects (fa), as follows:

$$F1 = 2 \frac{\det * (1 - fa)}{\det + (1 - fa)}, \quad (0.1)$$

The neural network may be trained using conventional neural network training methods, such as stochastic gradient descent, the Adam optimization method with cross-entropy loss function, or Dice loss function. Also, the weighted sum of a loss function mentioned above may be used. For better training of dangerous object detection, the input from the dangerous object map loss function may be included into the total loss function with a selected coefficient.

Segmentation of a Human Body

After the objects have been detected, the algorithm has to determine the body areas that contain dangerous or unknown objects. This can be done by a neural network trained to segment a human body into areas by assigning area indexes to each pixel in the image. For example, the following areas may be distinguished: 0—background, 1—head, 2—upper body, 3—lower body, 4—left arm, 5—right arm, 6—left leg, 7—right leg.

The method of data preparation is the same as illustrated by FIG. 3 and FIG. 5. The difference is that smaller images are used for segmentation, as body part segmentation doesn't have to be pixel-perfect.

The data may be obtained both through manual marking by experts and using the auxiliary algorithms following the flowchart in FIG. 5. In order to augment training images, horizontal mirroring, scaling and intensity changes may be used.

An architecture that is close to the sample in FIG. 8 can be used for body part segmentation. It is discussed in details above. Less number of layers and filters can be used in segmentation task.

The network comprises convolutional layers, ELU activations and maximum pooling in the first half, where pooling results in gradual decrease of dimensions of characteristics and increase of their channel quantities (see FIG. 8). Long skip connections and indexes of maximum elements from the pooling layers are passed from the left half of the network to its right half. The right half of the network is symmetrical to its left half and comprises convolutional layers, ELU activations and upsampling operations.

Figure 9:
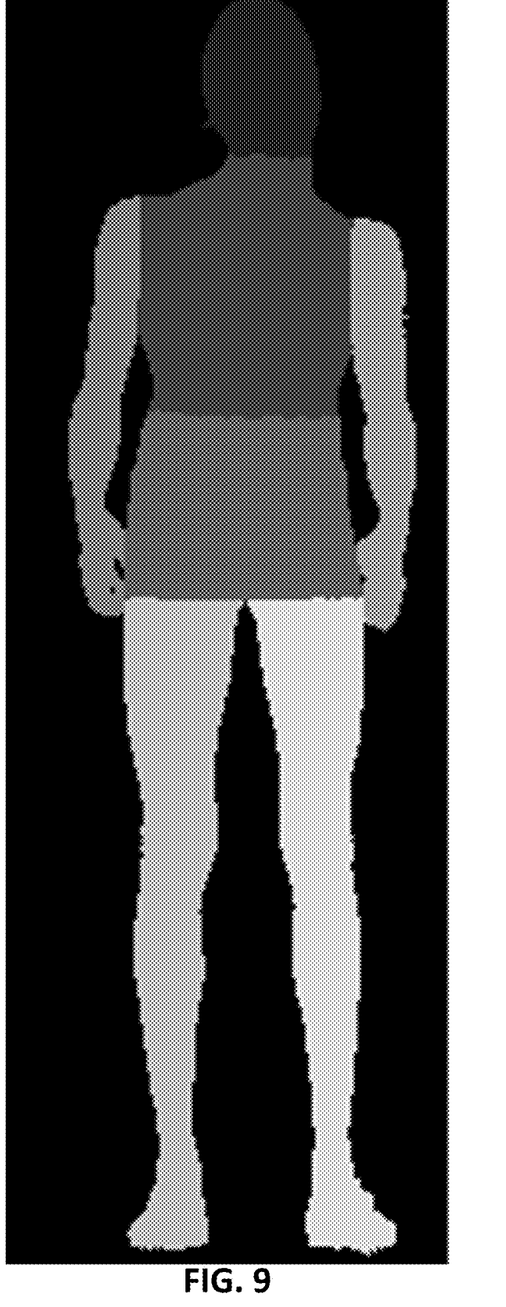
FIG. 9 is a sample of human body segmented into areas for X-ray imaging.

The output of the neural network contains an image with the number of channels corresponding to the number of body areas. This image should be processed using the SoftMax function that calculates each pixel's probability to belong to a certain body area. Each pixel is assigned to the higher probability area. Thus, a body part map is obtained. FIG. 9 is a sample of this map. The network may be trained using conventional neural network training methods, such as stochastic gradient descent, the Adam optimization method with cross-entropy loss function, or Dice loss function. Also, the weighted sum of a loss function mentioned above may be used.

Figure 10:
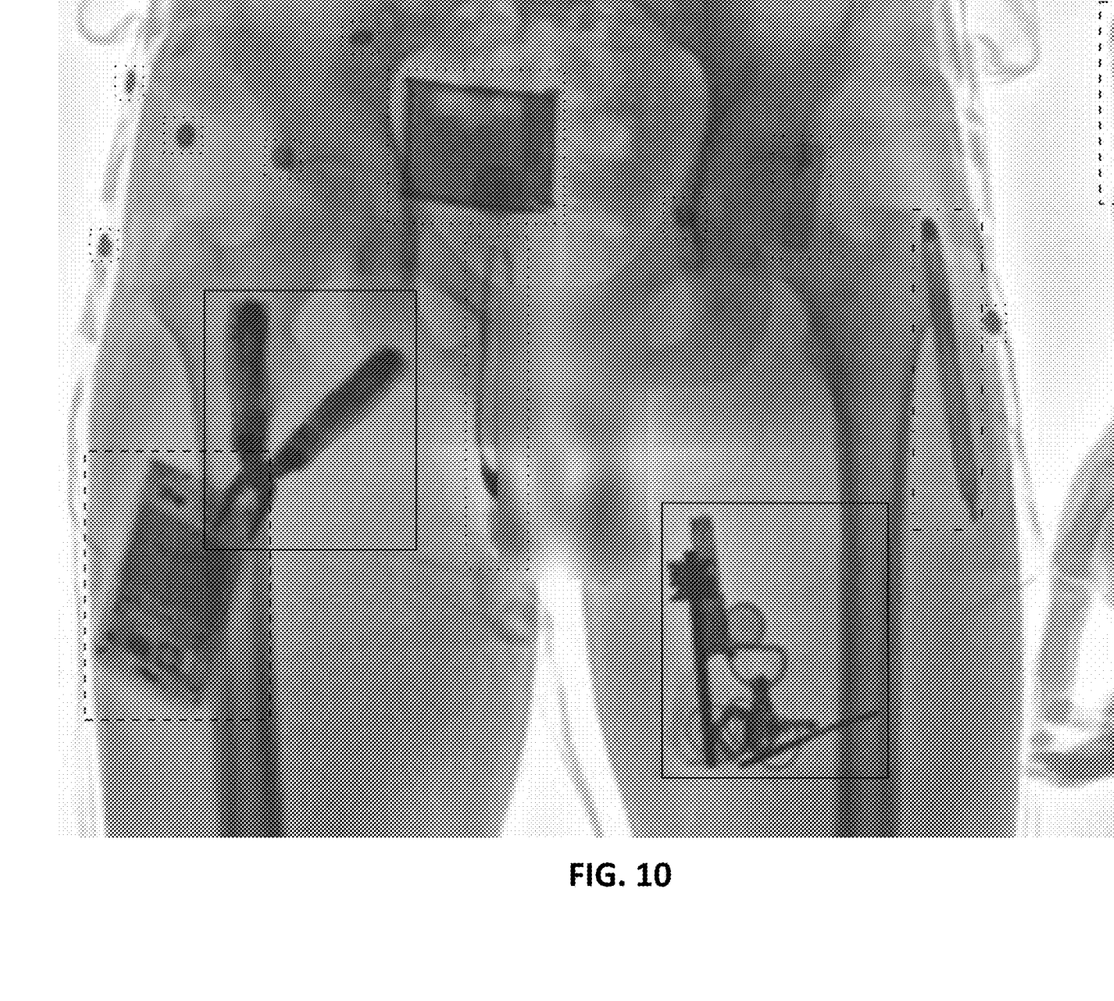
FIG. 10 shows a final result of the object search in the image.

Then, each body area is associated with a threat level depending on the types of objects that have been detected there. For instance, if a given body area contains dangerous objects, the operator is notified that this area is dangerous. FIG. 10 shows a final result of the object search in the image.

Figure 11:
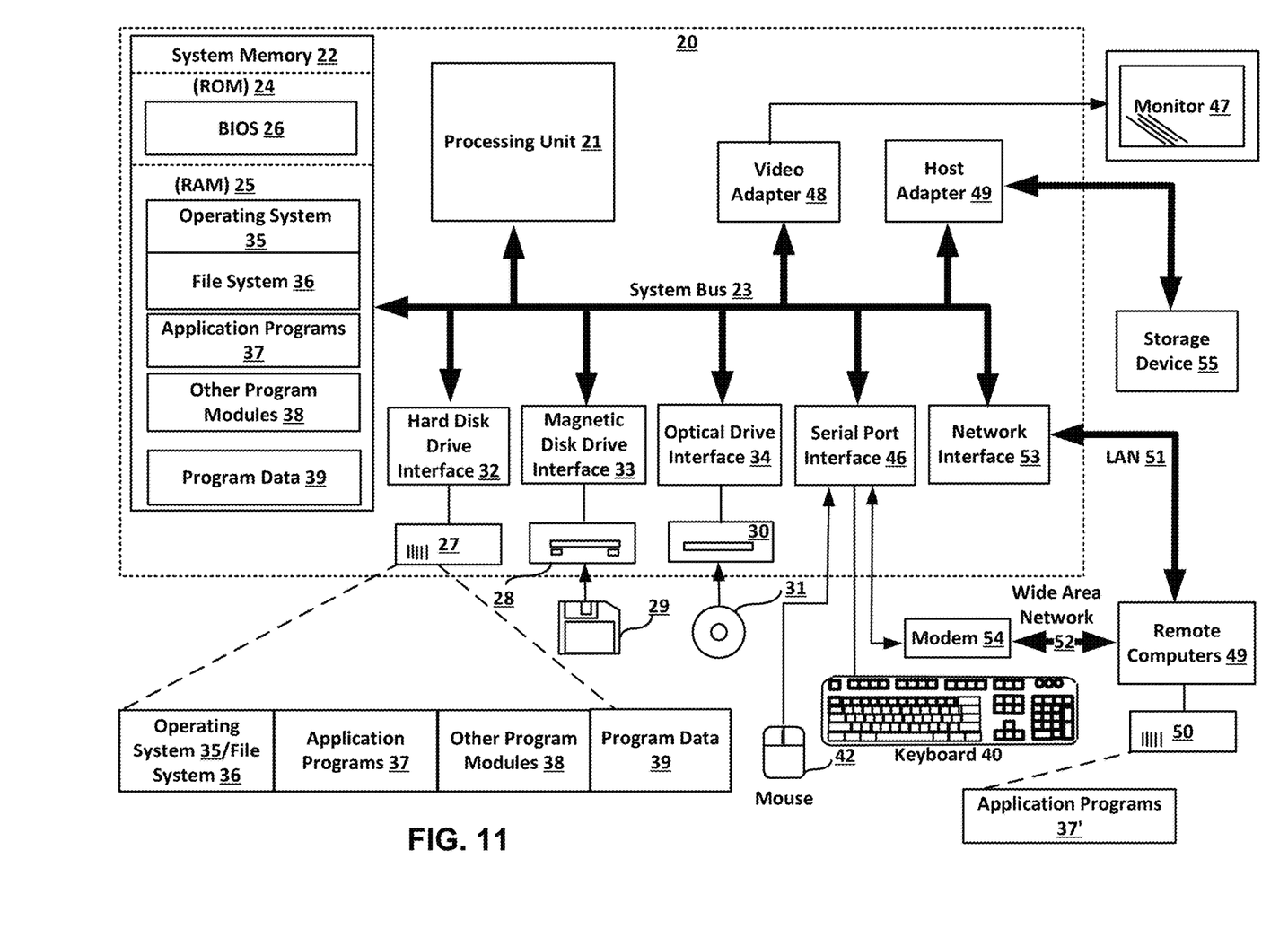
FIG. 11 shows an exemplary computer system or workstation used by the operator for implementing some aspects of the invention.

With reference to FIG. 11, an exemplary system for implementing the invention includes a general purpose computing device in the form of a host computer or a server 20 or the like, including a processing unit (CPU) 21, a system memory 22, and a system bus 23 that couples various system components including the system memory to the processing unit 21.

The system bus 23 may be any of several types of bus structures including a memory bus or memory controller, a peripheral bus, and a local bus using any of a variety of bus architectures. The system memory includes a read-only memory (ROM) 24 and random access memory (RAM) 25. A basic input/output system 26 (BIOS), containing the basic routines that help to transfer information between the elements within the computer 20, such as during start-up, is stored in ROM 24.

The computer or server 20 may further include a hard disk drive 27 for reading from and writing to a hard disk, not shown herein, a magnetic disk drive 28 for reading from or writing to a removable magnetic disk 29, and an optical disk drive 30 for reading from or writing to a removable optical disk 31 such as a CD-ROM, DVD-ROM or other optical media. The hard disk drive 27, magnetic disk drive 28, and optical disk drive 30 are connected to the system bus 23 by a hard disk drive interface 32, a magnetic disk drive interface 33, and an optical drive interface 34, respectively.

The drives and their associated computer-readable media provide non-volatile storage of computer readable instructions, data structures, program modules and other data for the server 20. Although the exemplary environment described herein employs a hard disk (storage device 55), a removable magnetic disk 29 and a removable optical disk 31, it should be appreciated by those skilled in the art that other types of computer readable media that can store data that is accessible by a computer, such as magnetic cassettes, flash memory cards, digital video disks, Bernoulli cartridges, random access memories (RAMs), read-only memories (ROMs) and the like may also be used in the exemplary operating environment.

A number of program modules may be stored on the hard disk (storage device 55), magnetic disk 29, optical disk 31, ROM 24 or RAM 25, including an operating system 35 (e.g., MICROSOFT WINDOWS, LINUX, APPLE OS X or similar). The server/computer 20 includes a file system 36 associated with or included within the operating system 35, such as the Windows NT™ File System (NTFS) or similar, one or more application programs 37, other program modules 38 and program data 39. A user may enter commands and information into the server 20 through input devices such as a keyboard 40 and pointing device 42.

Other input devices (not shown) may include a microphone, joystick, game pad, satellite dish, scanner or the like. These and other input devices are often connected to the processing unit 21 through a serial port interface 46 that is coupled to the system bus, and they may also be connected by other interfaces, such as a parallel port, game port or universal serial bus (USB). A monitor 47 or other type of display device is also connected to the system bus 23 via an interface, such as a video adapter 48. In addition to the monitor 47, computers typically include other peripheral output devices (not shown), such as speakers and printers. A host adapter 49 is used to connect to the storage device 55.

The server/computer 20 may operate in a networked environment using logical connections to one or more remote computers 49. The remote computer (or computers) 49 may be another personal computer, a server, a router, a network PC, a peer device or other common network node, and it typically includes some or all of the elements described above relative to the server 20, although here only a memory storage device 50 with application software 37' is illustrated. The logical connections include a local area network (LAN) 51 and a wide area network (WAN) 52. Such networking environments are common in offices, enterprise-wide computer networks, Intranets and the Internet.

In a LAN environment, the server/computer 20 is connected to the local network 51 through a network interface or adapter 53. When used in a WAN networking environment, the server 20 typically includes a modem 54 or other means for establishing communications over the wide area network 52, such as the Internet.

The modem 54, which may be internal or external, is connected to the system bus 23 via the serial port interface 46. In a networked environment, the program modules depicted relative to the computer or server 20, or portions thereof, may be stored in the remote memory storage device. It will be appreciated that the network connections shown are merely exemplary and other means of establishing a communications link between the computers may be used.

Having thus described a preferred embodiment, it should be apparent to those skilled in the art that certain advantages of the described method and apparatus have been achieved.

It should also be appreciated that various modifications, adaptations, and alternative embodiments thereof may be made within the scope and spirit of the present invention. The invention is further defined by the following claims.

REFERENCES

Abedini, M. et al., U.S. Pat. No. 9,684,967 B2, Imaging segmentation using multi-scale machine learning approach (2017).

Badrinarayanan, V. et al., *Segnet: A deep convolutional encoder-decoder architecture for image segmentation*. IEEE transactions on pattern analysis and machine intelligence, 39(12), 2481-2495 (2017).

Castano, G. V. et al., U.S. patent Ser. No. 10/002,313 B2, Deeply learned Convolutional Neural Networks (CNNS) for object localization and classification (2018).

Kumar, P. et al., *U-SegNet: Fully Convolutional Neural Network based Automated Brain tissue segmentation Tool*, arXiv preprint arXiv:1806.04429 (2018).

Mery, D., Automated Detection of Welding Discontinuities without Segmentation, *Materials Evaluation*, P. 657-663 (2011).

Montabone, S. et al., (2010), Human detection using a mobile platform and novel features derived from a visual saliency mechanism, *Image and Vision Computing*, V. 28(3), P. 391-402.

Piatrou, Vadzim A. et al., U.S. Pat. No. 9,576,219 B2, "Method and system for detection of contraband narcotics in human digestive tract." (2017).

Ronneberger, O. et al., *U-net: Convolutional networks for biomedical image segmentation*. In International Conference on Medical image computing and computer-assisted intervention (pp. 234-241). Springer, Cham (2015, October).

Saisan, P., U.S. Pat. No. 8,437,556 B1, Shape-based object detection and localization system (2013).

Sun, J. et al., U.S. Pat. No. 7,940,985 B2: Salient object detection (2011).

Sun, J. et al., U.S. Pat. No. 9,858,496 B2: Object detection and classification in images (2018).

Vaidya, N. M., U.S. Pat. No. 8,774,461 B2, Method and system for automatic detection of a class of objects (2014).

Yu, Z. et al., *A fast and adaptive method for image contrast enhancement*, paper presented at Image Processing, ICIP '04, International Conference, 24-27, Oct. 2004.

Zuiderveld, K., *Contrast Limited Adaptive Histograph Equalization*, in Graphic Gems IV, pp. 474-485, Academic Press Professional, San Diego (1994).

What is claimed is:

1. A method for detecting and recognizing hidden objects on a human body, the method comprising:

acquiring an incoming X-ray image of the human body passing through a penetrating X-ray scanner;

generating additional images based on the incoming image by performing logarithmic or saliency transformations or contrasting of the incoming X-ray image;

obtaining maps for all objects and known object classes, wherein the maps show which pixels correspond to objects and which pixels correspond to background, by passing the incoming X-ray image and the additional images through a neural network with a deep Segnet-U-Net architecture that is optimized for overlapping object detection with long skip connections before each downsampling layer of the neural network;

using the maps, identifying unknown objects in the incoming X-ray image by recognizing all objects and objects of known classes, and excluding previously classified objects from the known classes from an entire set of segmented non-anatomic areas;

segmenting the incoming X-ray image into multiple parts; and identifying parts containing objects belonging to both the known and to unknown classes.

2. The method of claim 1, wherein the neural network is trained by:

using a dataset of images of people passing through the penetrating X-ray scanner and/or a different penetrating X-ray scanner;

generating additional images from the dataset of images by performing the logarithmic or saliency transformations of the dataset of images;

adding logarithmic brightness values of images of the dataset of images containing individual objects to logarithmic brightness values of original human images in order to enlarge the dataset of images with forbidden objects;

using parts of the original human images to train the neural network to improve recognition of objects;

using the neural network with the deep Segnet-U-Net architecture to identify known and unknown objects and the classes to which they belong; and training the neural network using the dataset of images and maps for all objects and known classes in order to detect and classify previously unidentified classes of objects.

3. The method of claim 2, further comprising using only those parts of images of human bodies that contain objects and excluding empty areas for neural network training in order to enhance the detection of objects on human bodies.

4. The method of claim 1, further comprising using inpainting to conceal objects belonging to the known classes when displaying to an operator.

5. The method of claim 1, further comprising separating the additional images into anatomic and non-anatomic areas so that only human body contours and foreign objects are displayed, while concealing the human body itself.

6. The method of claim 5, wherein the separating uses segmentation of the additional images into separate anatomic areas so as to identify human body parts containing objects belonging to a class of prohibited objects.

* * * * *